(12) United States Patent
Stampa Diez del Corral et al.

(10) Patent No.: US 6,440,459 B1
(45) Date of Patent: Aug. 27, 2002

(54) PAROXETINE MALEATE POLYMORPH AND PHARMACEUTICAL COMPOSITIONS CONTAINING IT

(75) Inventors: Alberto Stampa Diez del Corral, Barcelona; Jordi Bosch Lladó, Gerona; Elias Molins Grau, Sant Feliu de Llobregat; Maria del Carmen Onrubia Miguel, Barcelona, all of (ES)

(73) Assignee: Medichem, S.A., Barcelona (ES)

( * ) Notice: Subject to any disclaimer, the term of this patent is extended or adjusted under 35 U.S.C. 154(b) by 0 days.

(21) Appl. No.: 09/743,047

(22) PCT Filed: Jul. 5, 1999

(86) PCT No.: PCT/ES99/00209

§ 371 (c)(1),
(2), (4) Date: Jan. 4, 2001

(87) PCT Pub. No.: WO00/01693

PCT Pub. Date: Jan. 13, 2000

(30) Foreign Application Priority Data

Jul. 7, 1998 (ES) ................................... 9801426

(51) Int. Cl.[7] ............................ A61K 9/20; A61K 9/22; A61K 9/28; A61K 9/48; A61K 9/52
(52) U.S. Cl. ..................... 424/474; 424/464; 424/465; 424/468; 424/451; 424/452
(58) Field of Search ................................ 424/489, 464, 424/465, 468, 451, 452, 474

(56) References Cited

U.S. PATENT DOCUMENTS

| 4,007,196 A | 2/1977 | Christensen et al. |
| 5,672,612 A | 9/1997 | Ronsen et al. |

FOREIGN PATENT DOCUMENTS

| CA | 2187128 | 4/1998 |
| EP | 0 188 081 A2 | 7/1986 |
| EP | 0 223 403 B1 | 5/1987 |
| EP | 0 269 303 A2 | 6/1988 |
| EP | 0 810 224 A1 | 12/1997 |
| WO | WO 96/24595 | 8/1996 |

Primary Examiner—Thurman K. Page
Assistant Examiner—Rachel M. Bennett
(74) Attorney, Agent, or Firm—Scully, Scott, Murphy & Presser

(57) ABSTRACT

The form B of paroxetine maleate polymorph is characterized by determined data of X ray diffraction: it has a chemical stability which is superior to that of the form A of paroxetine maleate. This superior stability enables to use the new polymorph for the fabrication of medicaments intended to the treatment of troubles related to dysfunctions of the central nervous system. The process for producing the paroxetine maleate comprises the preparation of paroxetine maleate solution and a consequent precipitation.

9 Claims, 2 Drawing Sheets

PAROXETINE MALEATE POLYMORPH AND PHARMACEUTICAL COMPOSITIONS CONTAINING IT

This Application is a 371 of PCT/ES99/00209 filed Jul. 5, 1999.

FIELD OF THE INVENTION

The present invention relates to a paroxetine maleate polymorph and to pharmaceutical formulations containing it; it also relates to the use and to a process for the preparation thereof. This polymorph is crystalline and is used as stable active principle in the preparation of pharmaceutical formulations indicated for disorders deriving from dysfunction of the central nervous system.

PRIOR ART REFERENCE

Paroxetine maleate, corresponding chemically to the (3S-trans)-3-[(1,3-benzodioxol-5-yloxy)methyl]-4-(4-fluorophenyl)piperidine acid maleate of formula

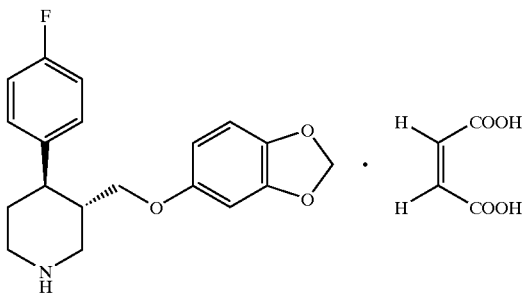

is described, together with a process for the preparation thereof, in Example 2 of U.S. Pat. No. 4,007,196 and in the same example of the corresponding Spanish patent of introduction ES-A-504997.

It is well known that paroxetine and the pharmaceutically acceptable salts thereof have a recognized activity as agents for the treatment of disorders related with dysfunction of the central nervous system, mainly, although not only, as antidepressants.

Owing to its poor handling properties, paroxetine base, is rather unsuitable for the preparation of pharmaceutical formulations and, up to date, has only been able to be used in practice in pharmaceutical formulations, as a paroxetine salt, namely, paroxetine hydrochloride. Thus, subsequent to the above mentioned U.S. patent, priority of which dates from 1974, the present inventors are unaware of the description or public use of paroxetine maleate in pharmaceutical formulations having commercial significance. On the contrary, there are numerous published patents and patent applications propounding the pharmaceutical use of paroxetine hydrochloride, both amorphous and in the non-hydrated and semi-hydrated crystalline forms thereof, among which there may be cited as examples EP-A-0188081, EP-A-0223403, WO-A-96/24595, EP-A-0810224 and U.S. Pat. No. 5,672,612, and there are numerous academic and scientific publications on the matter.

This is due to the fact that paroxetine maleate previously described in the documents U.S. Pat. No. 4,007,196 and ES-A-504997 is prepared in a form that will, hereinafter, be called Form A, which is substantially chemically unstable, which means that it undergoes degradation with time, which is a serious problem for any pharmaceutical formulation containing it.

There still exists, therefore, the need to having access to new pharmaceutically acceptable salts of paroxetine which may conveniently be used as an alternative to the different types of hydrochlorides described.

SUMMARY OF THE INVENTION

The object of the present invention is a new crystalline polymorph of paroxetine maleate, hereinafter called Form B, characterized in that it shows, substantially, the X-ray diffraction data given below in Table 1.

This Form B has superior stability properties; the invention also relates to a process for the preparation thereof.

Also object of the present invention are the pharmaceutical formulations containing the said new paroxetine maleate polymorph and the use of said polymorph in the manufacture of drugs against disorders related with dysfunction of the central nervous system.

DESCRIPTION OF THE INVENTION

Figure 2:
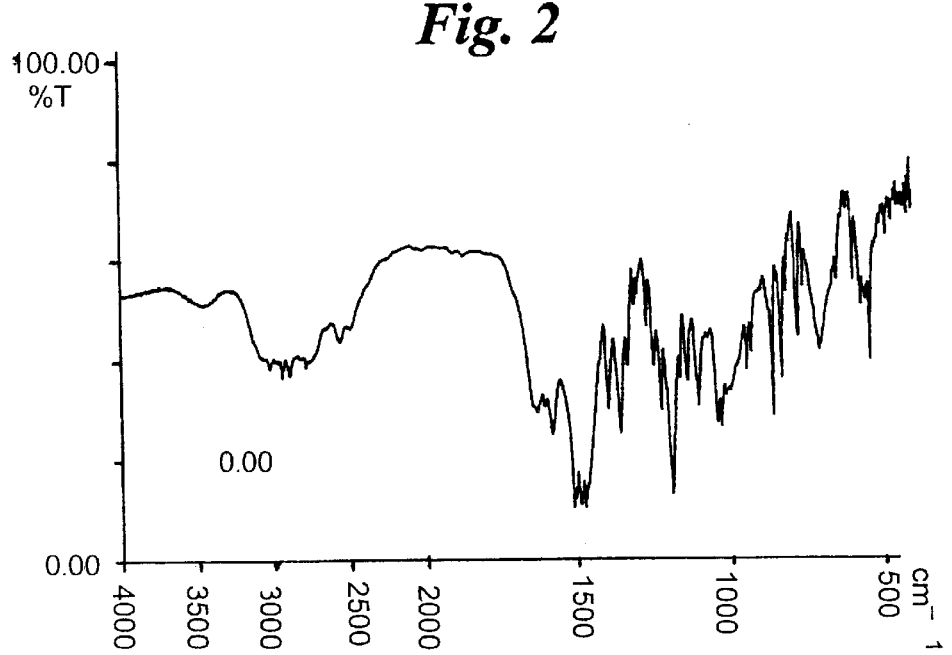
FIG. 2 is an IR spectrum of the new Form B polymorph of paroxetine maleate of the present invention, with KBr tablet.
Figure 4:
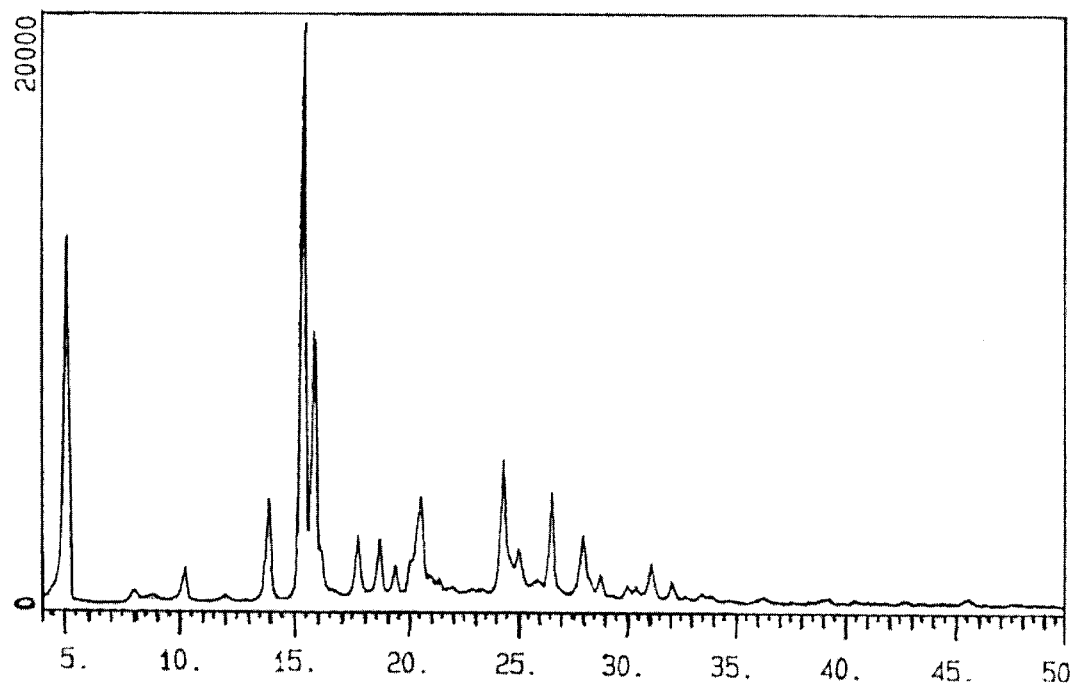
FIG. 4 is an X-ray diffraction diagram of the said new Form B polymorph, with a diffraction angle coverage ranging from 40° to 50° and steps of 0.02°.

The present invention has allowed a new polymorph of paroxetine maleate, Form B, to be prepared, whose IR spectrum, in KBr tablet, is given in FIG. 2 and whose X-ray diffraction diagram, with a diffraction angle coverage ranging from 4° to 50° and steps of 0.02°, is given in FIG. 4.

Table 1 gives the spacings "d" in Å and the relative intensities I(%) of the X-ray diffraction diagram in numerical form, for the peaks with relative intensities equal or superior to 5%.

Table 1. X-ray diffraction data of the Form B of paroxetine maleate.

TABLE 1

| X-ray diffraction data of the Form B of paroxetine maleate. | |
|---|---|
| D | I(%) |
| 17.11 | 63 |
| 8.61 | 5 |
| 6.35 | 18 |
| 5.73 | 100 |
| 5.57 | 46 |
| 4.99 | 11 |
| 4.74 | 11 |
| 4.57 | 7 |
| 4.32 | 19 |
| 3.65 | 25 |
| 3.54 | 10 |
| 3.35 | 20 |
| 3.18 | 12 |
| 3.09 | 8 |
| 2.87 | 7 | d = spacing in Å; I(%) = relative intensity ≧ 5%

Figure 1:
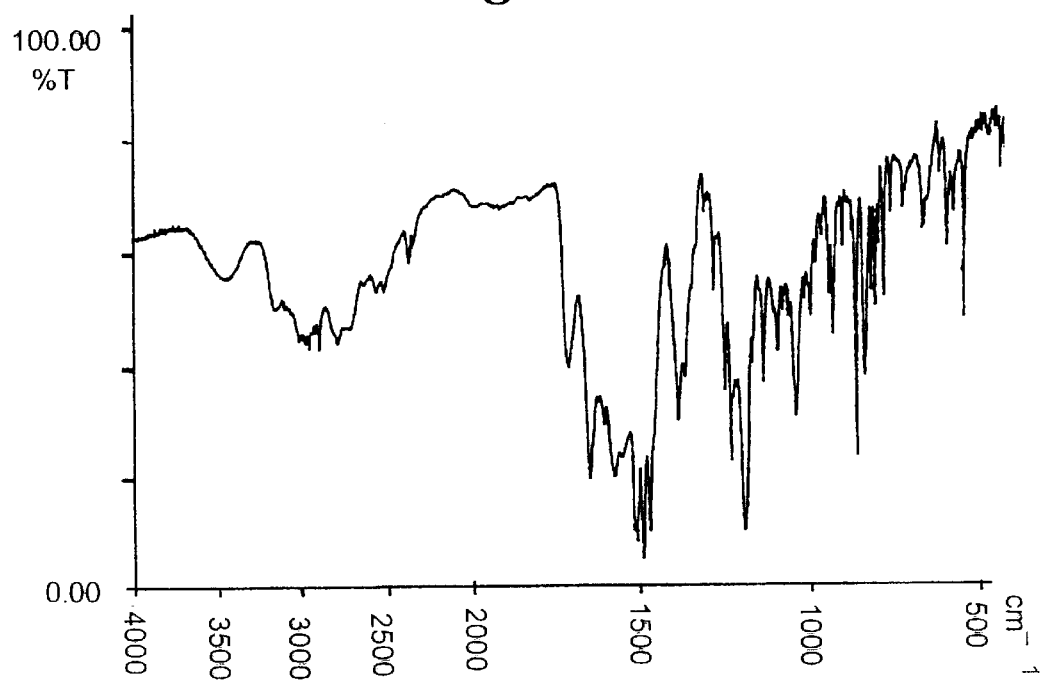
FIG. 1 is an IR spectrum of the Form A polymorph of paroxetine maleate, with KBr tablet.
Figure 3:
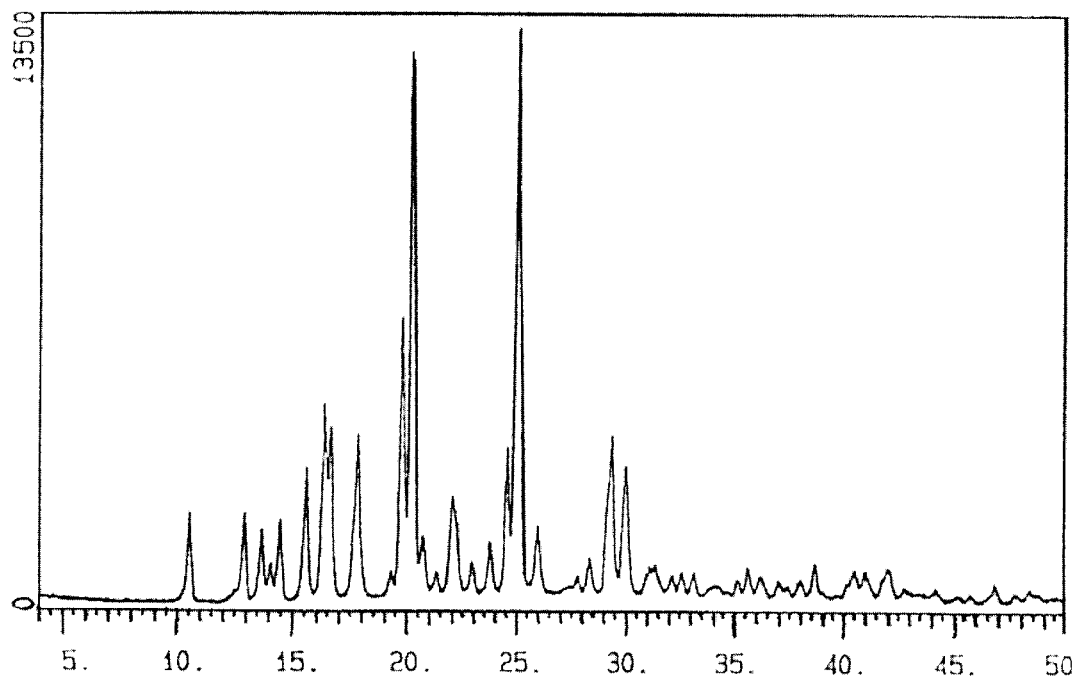
FIG. 3 is an X-ray diffraction diagram of the said Form A polymorph, with a diffraction angle coverage ranging from 4° to 50° and steps of 0.02°.

In turn, the IR spectrum and the X-ray diffraction diagram corresponding to the paroxetine maleate polymorph prepared according to the process described in Example 2 of the documents U.S. Pat. No. 4,007,196 and ES-A-504997, Form A, obtained under the same conditions, are given, respectively, for comparative purposes, in FIGS. 1 and 3, and the spacings "d" in Å and the relative intensities I(%) of the X-ray diffraction diagram are given in numerical form in Table 2, for the peaks with relative intensities equal or superior to 5%.

Table 2. X-ray diffraction data of the Form A of paroxetine maleate.

TABLE 2

X-ray diffraction data of the Form A of paroxetine maleate.

| d | I(%) |
|---|---|
| 8.35 | 16 |
| 6.81 | 16 |
| 6.45 | 12 |
| 6.28 | 7 |
| 6.09 | 15 |
| 5.66 | 23 |
| 5.39 | 33 |
| 5.30 | 31 |
| 4.96 | 28 |
| 4.47 | 49 |
| 4.37 | 91 |
| 4.01 | 17 |
| 3.87 | 6 |
| 3.74 | 10 |
| 3.62 | 25 |
| 3.54 | 100 |
| 3.43 | 12 |
| 3.06 | 13 |
| 3.04 | 28 |
| 2.97 | 23 | d = spacing in Å; I(%) = relative intensity ≥ 5%

The present inventors have surprisingly found that the Form B of paroxetine maleate is substantially more stable that the previously known Form A, allowing it to be effectively used in the preparation and manufacture of pharmaceutical formulations, Accelerated stability tests, i.e., keeping the product specimens under high temperature and humidity conditions, show an absence of significant degradation of Form B for periods of up to six months, while the Form A specimens evidence a notable degradation in the same period of time, with the apparition of by-products originated thereby.

A further additional advantage of the Form B consists in it showing a better behavior with regard to filtration that the Form A, since it retains a smaller amount of solvent and the drying process is simplified.

Form B may be prepared from a solution of paroxetine maleate in a solvent or mixture of solvents, with precipitation therefrom, using techniques within the reach of the man of the art, of the desired crystalline polymorph.

The starting paroxetine maleate solution may be prepared:
a) by salification of a solution of paroxetine base in a solvent or a mixture of solvents, by addition of maleic acid or of a salt thereof which may be displaced by paroxetine base, or
b) by dissolving the previously prepared Form A of paroxetine maleate in the solvent or mixture of solvents The solvents may be any type of those regularly used in chemical synthesis, with the sole limitation that the Form B polymorph of paroxetine maleate may be isolated from said solvents. Among said type of solvents there may be mentioned the low or high boiling point alcohols, such as methanol, ethanol, 1-propanol, 2-propanol, ethylene glycol, etc.; the ketones, such as acetone, propanone, 2-butanone, methylisobutylketone, etc.; the esters, such as the alkyl acetates; the aliphatic or aromatic hydrocarbons, such as n-hexane, benzene, toluene, xylenes, etc.; the non-cyclic or cyclic ethers, such as ethyl ether, tetrahydrofuran, 1,4-dioxane, etc.; the chlorinated hydrocarbons, such as methylene chloride, chloroform, carbon tetrachloride, perchloroethylene, etc.; alkylamides, such as dimethylformamide and dimethylacetamide; and mixtures of said solvents and/or with water.

The preferred solvents for the purposes of the present invention are the short chain aliphatic alcohols and/or mixtures thereof with aromatic hydrocarbons, being particularly preferred 2-propanol and/or mixtures of 2-propanol and toluene.

When paroxetine maleate is formed "in situ" in the solution, it is preferred to use 2-propanol as solvent and when the solution is prepared from the Form A, it is preferred to use a mixture of 2-propanol and toluene in volumetric proportions ranging from 10:90 to 90:10, preferably from 35:65 to 85:15.

Variable concentrations of the paroxetine maleate solution may be used, concentrations ranging from 150 g/L to 250 g/L being preferred.

The Form B of paroxetine maleate is precipitated from the solution by any of the techniques known to the man of the art, among which the most usual is gradually to cool the solution to within a temperature gradient sufficiently broad as to produce a solubility differential of the Form B in the solvent system between the upper and lower temperatures of said gradient.

Conveniently, although not necessarily, crystallization of the Form B may be stimulated by seeding with previously formed pure Form B crystallization nuclei.

The published patents and patent applications EP-A-0188081, EP-A-0223403, WO-A-96/24595, EP-A-0810224 and U.S. Pat. No. 5,672,612, incorporated herein by reference, describe in detail the types of disorders, related with dysfunction of the central nervous system, for the treatment of which paroxetine hydrochloride is indicated. Since the therapeutic action is bound to the paroxetine itself and not to its salts, which serve only as a vehicle therefor, the paroxetine maleate Form B of the present invention has the same type of therapeutic activity and at dose levels similar to those described.

Furthermore, the Form B polymorph of paroxetine maleate may be used for the preparation of pharmaceutical formulations of different types, since it has excellent stability and handling characteristics, by association thereof with acceptable pharmaceutical excipients well known to the man of the art. As far as ways of administration, excipients and other additives are concerned, said pharmaceutical formulations are fully similar to those also described in detail in the above mentioned patents, also incorporated herein by reference for said aspects, only replacing in the pharmaceutical formulations described in said patents the different forms of paroxetine hydrochloride to which they refer by the Form B of paroxetine maleate of the present invention.

Although the Form B of paroxetine maleate is appropriate for any type of pharmaceutical form, in view of the ease of administration thereof, the oral forms such as pills, tablets and capsules are preferred. Said oral forms may be prepared by conventional techniques, well known to the man of the art, using the regular excipients such as, for example, different forms of starch and derivatives thereof, stearates, microcrystalline cellulose, alkyl cellulose polymers, polymers type PVP, etc. If desired, the tablets may be coated with protective films, by the use of conventional techniques.

With a view to providing the man of the art with an understanding of the present invention, and without them being understood to represent limitations of the subject matter thereof, the following examples are provided.

EXAMPLES

Example 1
Preparation of Paroxetine Maleate Form A

Paroxetine maleate Form A was prepared following the method described in Example 2 of U.S. Pat. No. 4,007,196. It had an infra red spectrum in solid state (KBr) and a X-ray diffraction diagram in powder conforming to those shown in FIGS. 1 and 3 and in Table 2.

Example 2
Preparation of Paroxetine Maleate Form B, from Paroxetine Base 10 g (30.36 mmoles) of paroxetine base were dissolved in 50 mL of 2-propanol in a 250 mL flask provided thermometer, magnetic stirring, addition funnel and refrigerant. The mixture was heated to 40° C. and the addition of a solution formed by 4.402 g (37.9 mmoles) of maleic acid in 22 mL of 2-propanol was started, the addition being maintained gradually over a period of 25 minutes. The salt formed started to precipitate approximately one minute after completion of the addition. The temperature was held at 40° C. for 30 minutes, the mass was allowed to cool to room temperature (20° C.), stirring was continued for a further 1 hour at this temperature, it was filtered and the product was washed with isopropanol over the filter itself. The product obtained was dried at 50° C. and under a vacuum below 50 mm Hg. 11.54 g of paroxetine maleate Form B (yield 85.3%) were obtained, having an infra red spectrum in solid state (KBr) and a X-ray diffraction diagram in powder conforming to those given in FIGS. 2 and 4 and in Table 1.

Example 3
Preparation of Paroxetine Maleate Form B, from Paroxetine Maleate Form A 10 g of paroxetine maleate Form A, 12.5 mL of toluene and 37.5 mL of 2-propanol were charged in a 250 mL flask provided with mechanical stirring under pressurized nitrogen. The resulting white suspension was heated until a solution was formed, it being observed that all the product had already dissolved between 55° C. and 65° C. Heating was withdrawn and the solution was allowed to cool gradually. When the temperature reached 44° C., the solution was seeded with a small amount of paroxetine maleate Form B crystals. When the temperature reached 40° C., the massive precipitation of a heavy solid started and, once a temperature of 25° C. had been reached, stirring was continued for a further 1 hour. The precipitated product was filtered, washed on the filter with 5 mL of 2-propanol and was dried at 50° C. and under a vacuum lower than 50 mm Hg, to provide 9.12 g of paroxetine maleate Form B (yield 91.2%) having an infra red spectrum in solid state (KBr) and a X-ray diffraction diagram in powder conforming to those given in FIGS. 2 and 4 and in Table 1.

Example 4
Accelerated Stability Tests

Samples of paroxetine maleate Form A and Form B were packaged in two-ply polythene bags and stored at 40° C. and 75% Relative Humidity. The samples were analyzed at the time of packaging by HPLC and were analyzed with the same technique at the end of one month and six months of storage. Form B was observed to be substantially unaltered both at the end of one month and at the end of six months, whereas on the contrary, Form A showed clear signs of degradation at the end of one month, since new impurities appeared and the proportion of some of those existing in the original sample notably increased. At the end of six months, Form A evidenced a high degree of degradation relative to the initial product.

Example 5
Pharmaceutical Formulation for Tablets

Tablets containing the following ingredients in the formulation thereof for each unit were prepared by conventional mixing, granulation and pressing techniques:

Paroxetine maleate (Form B) . . . 27.05 mg

Starch sodium glycolate . . . 15.00 mg

Methyl cellulose 15 cps . . . 15.00 mg

Magnesium stearate . . . 3.00 mg

Dicalcium phosphate dihydrate . . . 239.95 mg

Example 6
Pharmaceutical Formulation for Tablets

Tablets containing the following ingredients in the formulation thereof for each unit were prepared by conventional mixing, granulation and pressing techniques:

Paroxetine maleate (Form B) . . . 27.05 mg

Sodium croscarmellose . . . 12.00 mg

Polyvinylpirrolidone K-30 . . . 10.00 mg

Magnesium stearate . . . 3.00 mg

Microcrystalline cellulose . . . 247.95 mg

Example 7
Pharmaceutical Formulation for Capsules

Capsules containing the following ingredients in the formulation thereof for each unit were prepared by conventional mixing, granulation and filling techniques, using n° 2 gelatine capsules:

Paroxetine maleate (form b) . . . 27.05 mg pregelatinized starch . . . 10.00 mg starch sodium glycolate . . . 8.00 mg magnesium stearate . . . 2.00 mg lactose monohydrate . . . 152.95 mg

What is claimed is:

1. Paroxetine maleate polymorph in Form B showing substantially the following X-ray diffraction data:

| d | l (%) |
|---|---|
| 17.11 | 63 |
| 8.61 | 5 |
| 6.35 | 18 |
| 5.73 | 100 |
| 5.57 | 46 |
| 4.99 | 11 |
| 4.74 | 11 |
| 4.57 | 7 |
| 4.32 | 19 |
| 3.65 | 25 |
| 3.54 | 10 |
| 3.35 | 20 |
| 3.18 | 12 |
| 3.09 | 8 |
| 2.87 | 7 | d = spacing in Å; l (%) = relative intensity ≧ 5% and an infra red spectrum in KBr tablet substantially coincident with the one shown in FIG. 2.

2. Pharmaceutical formulations containing the paroxetine maleate in Form B of claim 1, in association with excipients and other pharmaceutically acceptable additives.

3. A process for the preparation of paroxetine maleate in Form B of claim 1, wherein there is first prepared a solution of paroxetine maleate in a solvent or mixture of solvents and thereafter the paroxetine maleate in Form B of claim 1 is precipitated from said solution.

4. The process of claim 3, wherein the starting solution of paroxetine maleate is prepared by salification of a solution of paroxetine base in the solvent or mixture of solvents by addition of maleic acid or of a salt thereof displaceable by paroxetine base.

5. The process of claim 3, wherein the starting solution of paroxetine maleate is prepared by dissolving the previously obtained Form A paroxetine maleate in the solvent or mixture of solvents.

6. The process of at least one of claims 3 to 5, wherein the solvent or mixture of solvents is selected from among low or high boiling point alcohols, ketones, esters, aliphatic or aromatic hydrocarbons, non-cyclic or cyclic ethers, chlorinated hydrocarbons, alkylamides and water.

7. The process of claim 6, wherein the solvent or mixture of solvents is selected from among short chain aliphatic alcohols and/or mixtures thereof with aromatic hydrocarbons.

8. The process of claim 3, wherein the paroxetine maleate solution is seeded with crystallization nuclei of paroxetine maleate in Form B.

9. A process for preparing drugs for the treatment of disorders related with dysfunction of the central nervous system comprising adding a stable effective amount of the paroxetine in Form B of claim 1 to excipients and other pharmaceutically acceptable additives.

* * * * *